United States Patent [19]

Grollier

[11] Patent Number: 5,063,046

[45] Date of Patent: Nov. 5, 1991

[54] DENTIFRICE COMPOSITIONS HAVING ANTI-CARIES ACTIVITY AND CONTAINING A POLYCATIONIC POLYMER FLUORIDE

[75] Inventor: Jean-François Grollier, Paris, France

[73] Assignee: L'Oreal, Paris, France

[21] Appl. No.: 524,316

[22] Filed: May 17, 1990

[30] Foreign Application Priority Data

May 18, 1989 [FR] France ................... 89 06500

[51] Int. Cl.$^5$ .................. A61K 7/16; A61K 7/18; A61K 7/22; A61K 31/785
[52] U.S. Cl. .................. 424/52; 424/54; 424/78
[58] Field of Search .................. 424/52, 54

[56] References Cited

U.S. PATENT DOCUMENTS

| | | | |
|---|---|---|---|
| 4,110,083 | 8/1978 | Benedict | 51/295 |
| 4,157,387 | 6/1979 | Benedict | 424/54 |
| 4,205,143 | 5/1980 | Goodman | 525/213 |
| 4,390,689 | 6/1983 | Jacquet et al. | 528/335 |
| 4,837,007 | 6/1989 | Duckworth et al. | 424/52 |

FOREIGN PATENT DOCUMENTS 0200903 12/1986 European Pat. Off. .
0228209 7/1987 European Pat. Off. .

*Primary Examiner*—Shep K. Rose
*Attorney, Agent, or Firm*—Cushman, Darby & Cushman

[57] ABSTRACT

A dentifrice composition contains, as an anti-caries agent, at least one water-soluble polycationic polymer, containing units which contain at least one quaternized nitrogen which is part of the macrochain, and in which at least 5% of the cationic charges are balanced by fluoride anions; and use of such polycationic polymer fluorides as anti-caries agents.

22 Claims, No Drawings

DENTIFRICE COMPOSITIONS HAVING ANTI-CARIES ACTIVITY AND CONTAINING A POLYCATIONIC POLYMER FLUORIDE

BACKGROUND OF THE INVENTION

The present invention relates to new dentifrice compositions having anti-caries activity and containing a polycationic polymer fluoride.

In the following description, "dentifrice composition" is used to mean any solid or liquid composition intended for mouth hygiene, such as toothpaste, chewing gum, powder or mouthwash.

It is known that the use of products for cleaning teeth, and in particular dentifrice compositions, has for an essential object, insofar as the prevention of caries is concerned, the removal of dental plaque or the prevention of its formation. Dental plaque, which is composed of food residues transformed by bacterial metabolism, is a deposit which hardens and strongly adheres to the teeth if it is not rapidly removed. Dental plaque in turn promotes the multiplication of bacteria which transform sugars into acid products. These acid products attack tooth enamel and demineralize it. In the absence of treatment, the bacteria and their acid secretions can progressively reach the tooth pulp, going so far as to cause its destruction.

It is also known that dental plaque deposited on teeth and gums where they contact same plays an important role in various gum infections.

It is known that conventional dentifrice products which principally contain abrasive particles (polishing agents) and surface active agents (cleaning and foaming agents) do not provide sufficient removal of dental plaque and the prevention of caries.

In order to fight more effectively against caries, various bactericidal products capable of destroying or limiting to a great extent the populations of bacteria responsible for the formation of dental plaque have been proposed.

It must, however, be noted that the use of bactericidal agents poses formulation problems, since it is necessary to find bactericidal agents which are compatible both with the abrasive agent and with the surface active agent. These formulation difficulties are sufficiently great to have led researchers to recommend the successive use of two separate compositions, one containing the surface active agent and the other containing the bactericidal agent; see French Patent Application No. 75.26219 published under No. 2,282,861.

The prevention of caries has also been researched by attempting to use to advantage the properties of fluoride ions which are used in a small amount. It is generally agreed that fluoride ions have the effect of transforming the hydroxyapatite of tooth enamel into fluoroapatite, which increases the crystallinity and the hardness of the enamel and thus renders it more resistant to acid attack.

The use of metal fluorides, such as sodium fluoride and tin fluoride, in dentifrice compositions, has also been recommended. However, these fluorides have the disadvantage of low compatibility with conventional mineral polishing agents, in particular with alumina and calcium carbonate, contained in toothpastes, with the interactions between said fluorides and the polishing agents leading in particular to a decrease in the content of free fluoride ions and, therefore, to lower effectiveness.

In order to overcome these disadvantages, the use of monofluorophosphate, which is more compatible with polishing agents, has been proposed. However, even with the use of dentifrice products containing high amounts of fluorophosphate, the fixation of the fluoride ions onto the teeth remains fairly low due to the limited contact time between the dentifrice composition and the tooth.

However, monofluorophosphate does not act directly on the primary cause of caries, i.e., bacteria. This is the reason for which, with a view to increasing the effectiveness of the fluoride ions, anti-bacterial, anti-plaque agents have often been added to them.

It has also been proposed to apply on the teeth fluid materials, which are capable of hardening rapidly, so as to form a protective resin coating which can play the role of fluoride ion exchanger. However, such hardenable fluid compositions can, in practice, only be used on teeth which are already affected with caries and cannot be used for normal hygienic care in dentifrice compositions. In addition, the need to apply a non-hardened composition has various disadvantages due, in particular, to the toxicity of the monomer compounds and possibly of the polymerization initiators whose presence is necessary; see the article by B.R. Rawls and P.P. Zimmerman, Caries Res. 17:32–43 (1983).

DETAILED DESCRIPTION OF THE INVENTION

It has now been discovered that the fluorides of certain polycationic polymers containing recurrent units, which contain a quaternized nitrogen, can be incorporated into the dentifrice compositions as anti-caries agents.

It has also been discovered that the use of such fluorides is compatible with the use of mineral polishing agents which may be present in these compositions.

It could, in effect, be feared that these polycationic polymers would be adsorbed, and consequently inactivated, on the polishing agents which are used in a finely divided state and which therefore have a large contact surface. However, research by the applicant has provided the discovery that in the dentifrice compositions of the invention, the polycationic polymer fluorides, in spite of the presence of finely divided mineral polishing agents, remain active and provide protection against the demineralization of the teeth.

It has also been discovered that the polycationic polymer fluorides used in accordance with the present invention are compatible with conventional surface active agents used in the dentifrices, including anionic surface active agents.

On the other hand, these polycationic polymer fluorides have bactericidal activity which reinforces their activity against dental plaque and against caries.

In addition, it has been noted that the presence of polycationic polymer fluorides, in the dentifrice compositions of the present invention, delay the drying in air of said compositions and facilitate their preparation, in particular their homogenization.

The object of the present invention, therefore, is a dentifrice composition containing conventional ingredients of such a composition, characterized by the fact that it contains, as an anti-caries agent, at least one polycationic polymer fluoride comprising units which contain at least one quaternized nitrogen as part of the macrochain, with said polycationic polymer fluoride being soluble in water.

The conventional ingredients present in the dentifrice compositions, as well as the methods of preparing these compositions, are well known and are described, for example, in the following works: Handbook of Cosmetic Science, H. W. Hibbot Ed., Pergamon Press (Oxford, London, New York, Paris), and Harry's Cosmeticology, 6th Edition, Leonard Hill Books (London).

It is appropriate to note that the use in the present invention of the term "polycationic polymer fluoride" means not only polycationic polymers in which the cationic charges are totally balanced by fluoride ions, but also polycationic polymers in which at least 5% of the cationic charges are balanced with fluoride anions. Of course, the other cationic charges are balanced with other anions, in particular chloride ions and/or bromide ions.

In the compositions of the present invention, the concentration of polycationic polymer can vary in amounts ranging from 0.1 to 5% by weight relative to the total weight of the composition, and preferably from 0.5 to 5% by weight.

Preferably, the amount of fluoride ions is such that the concentration of fluoride ions does not exceed 500 ppm relative to the total weight of the composition.

It is, of course, possible to use in the compositions of the present invention mixtures of polycationic polymer fluorides. It is also possible to add other fluorinated derivatives thereto, such as, for example, alkaline metal fluorides or alkaline monofluorophosphates.

The polycationic polymer fluorides are prepared in accordance with conventional methods, for example starting from other halides (chlorides, bromides), in particular through ion exchange.

Of course, the polycationic polymers used in the compositions of the present invention are non-toxic polymers.

Representative polycationic polymers whose fluorides can be used in the compositions of the present invention, include, particularly, those in which each quaternized nitrogen atom of the macrochain has two lateral substituents selected from the substituted or unsubstituted aliphatic, hydroxyaliphatic, alicyclic or arylaliphatic groups, containing at most 20 carbon atoms, or indeed the two lateral substituents attached to a same nitrogen atom together comprise, with said atom, a ring capable of containing a second heteroatom other than nitrogen, or even two lateral substituents attached to two consecutive quaternized nitrogen atoms represent together a divalent group. In addition, in these polymers, two consecutive quaternized nitrogen atoms are, of course, connected by a divalent group forming, with said quaternized nitrogen atoms, the macrochain, with the said divalent group being in particular an alkylene or arylene group which is optionally substituted and capable of containing heteroatoms.

Among these polycationic polymers, there can in particular be cited those in which the macrochain is composed by the succession of two divalent groups, present alternately in the chain, each between two consecutive quaternized nitrogen atoms, with these two divalent radicals optionally being identical. It is known that such polymers form a known class of cationic polymers particularly containing ionenes.

In the present invention, unless stated to the contrary, the aliphatic groups, including the alkyl groups, and the corresponding divalent groups, including the alkylenes, most frequently have from 1 to 12 carbon atoms; the aryl (or arylene) groups most frequently have from 6 to 20 carbon atoms and are generally groups derived from phenyl (or phenylene), naphthyl (or naphthylene), or the arylene groups are bis-phenylene groups.

Among the polycationic polymers of the ionene type, there can be cited in particular, as a non-limiting example, those which contain, or are composed of the recurrent units of Formula I.

in which:

$R_1$, $R_2$, $R_3$ and $R_4$, which may be identical or different, represent optionally substituted aliphatic, alicyclic or arylaliphatic group containing at most 20 carbon atoms, or a hydroxyaliphatic group having from 1 to 8 carbon atoms; or even two substituents ($R_1$ and $R_2$) and/or ($R_3$ and $R_4$) attached to a same nitrogen atom can together represent a divalent group forming, with the nitrogen atom to which they are attached, a heterocycle capable of containing one or several heteroatoms other than nitrogen; or even the pairs ($R_1$ and $R_3$) and/or ($R_2$ and $R_4$) together form a divalent group connecting the two consecutive nitrogen atoms, represented in the unit of Formula I, to which they are respectively attached;

A and B, which may be identical or different, represent a linear or branched alkylene group having 2 to 20 carbon atoms, which may be unsaturated, with said alkylene group capable of being substituted and/or interrupted by one or several heteroatoms, and/or by one or several heteroatom groups and/or by one or several aliphatic or aromatic rings or by one or several heterocycles; a cycloalkylene group which may be substituted and/or optionally contain double bonds, capable of containing up to 20 carbon atoms; one or several arylene groups having 6 to 20 carbon atoms, with said arylene groups optionally being substituted and/or separated by one or several heteroatoms and/or by one or several heteroatom groups and/or by one or several alkylene groups and/or by one or several aliphatic rings and/or by one or several heterocycles;

and $X^-$ represents an anion, it being understood that, in a composition in accordance with the present invention, at least 5% in number of the anions present in the polycationic polymer, having the units of Formula I, are fluoride ions.

In the units of Formula I:

$R_1$ and/or $R_3$ represent, in particular, an alkyl or hydroxyalkyl group having 1 to 6 carbon atoms;

$R_2$ and/or $R_4$ represent, in particular, an alkyl or hydroxyalkyl group having, for example, 1 to 16 carbon atoms, or a cycloalkylalkyl (the cycloalkyl having 5 or 6 chains) or aralkyl (in particular phenylalkyl) group in which the alkyl moiety has, for example, 1 to 3 carbon atoms, or a cycloalkyl group with 5 or 6 chains;

or one or several $R_1$, $R_2$, $R_3$, $R_4$ groups represent a group

in which $R'_1$ represents —H or a lower alkyl group and $R'_2$ represents one of the following groups:

—CN, —CO—OR'₃, —CO—R'₃, —CO—N(R'₄)-₂, —CO—O—R'₅—Y and CO—NH—R'₅—Y,

R'₃ being a lower alkyl group, R'₆ being —H or a lower alkyl group, R'₅ being a lower alkylene, and Y being a quaternary ammonium group;

or, when two substituents (R₁ and R₂), or (R₃ and R₄), attached to a same nitrogen atom, comprise, with said atom, a heterocycle, they can represent together, in particular, a polymethylene group having 2 to 5 carbon atoms which are optionally substituted and/or interrupted by an oxygen heteroatom;

when the pair (R₁, R₃) and/or the pair (R₂, R₄) together form a divalent group, said divalent group is, in particular, an optionally unsaturated hydrocarbon group having 2 to 10 carbon atoms; for example the pairs (R₁, R₃) and/or (R₂, R₄) each represent an ethylene group (A and/or B then being preferably an ethylene group), or indeed the pairs R₁, R₃ and R₂, R₄ form with A (or with B) and with the nitrogen atoms to which they are attached a group

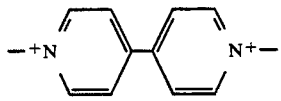

A and/or B represent in particular an alkylene group having for example 2 to 12 carbon atoms in the chain, which may be substituted (for example with one or several alkylene having 1 to 10 carbon atoms, and/or with one or several —OH or —O groups) and/or optionally interrupted with one or several arylene groups and/or with one or several heterocycles and/or with one or several heteroatoms or heteroatom groups such as —O—, —S—, —SO—, —SO₂—, —S—S—, —N(R₅)— or —N⁺(R₆)₂.X₁—, R₅ being a hydrogen or an alkyl having, for example, 1 to 12 carbon atoms, an aryl having 6 to 20 carbon atoms or an aralkyl (in particular phenylalkyl) in which the alkyl moiety contains 1 to 3 carbon atoms, R₆ being an alkyl having 1 to 10 carbon atoms, and X₁ — being an anion; for example A and/or B represent a group

—(CH₂)ₙ—Z—(CH₂)ₙ— where n represents an integer from 1 to 10 and Z represents for example a divalent group having the formula

—N(R₅)—CO—N(R₅)—

—N(R₅)—CO—Y₁—CO—N(R₅)

—N(R₅)—SO₂—(C₆H₄—C₆H₄—SO₂)ₚ—N(R₅)—

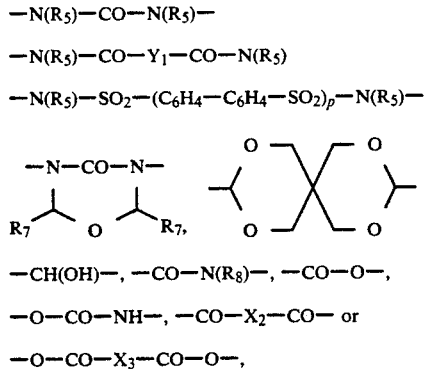

—CH(OH)—, —CO—N(R₈)—, —CO—O—,

—O—CO—NH—, —CO—X₂—CO— or

—O—CO—X₃—CO—O—, wherein
R₅ is defined as above,
R₇ has the same meaning as R₅,
R₈ represents H or a lower alkyl, Y₁ represents an alkylene (optionally interrupted by an —S—S— group), an alkenylene containing 4-20 carbon atoms, arylene, diaminoalkylene, diaminoarylene, dioxyalkylene, dioxyarylene, or polyoxyalkylene group, or a direct covalent bond, p is a number equal to 0 or 1, X₂ is a diaminoalkylene (with amino endings), dioxyalkylene or polyoxyalkylene (with oxy endings) group, or a dithioalkylene group (with thio endings) in which the alkylenes have 2 to 20 carbon atoms, X₃ is an alkylene, cycloalkylene or arylene, which may be substituted or unsubstituted, or a diaminoalkylene, diaminocycloalkylene or diaminoarylene;

or further Z represents an arylene group or several arylene groups optionally connected by a heteroatom or a heteroatom group, with Z, for example, being a group

—C₆H₄—, —C₆H₄—C₆H₄, —C₆H₄—O—C₆H₄—,

C₆H₄— SO₂—C₆H₄— or 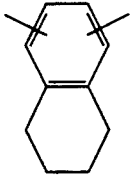

or further A and/or B represent a divalent —R₁—Y₂—R₂— group, in which R₁ and R₂ represent arylene groups and Y₂ represents a divalent aliphatic group (for example a linear or branched alkylene having 1 to 10 carbon atoms), which may be substituted (for example with one or several —OH or —O groups) and/or interrupted by one or several heteroatoms and/or by one or several heteroatom groups and/or by one or several heterocycles, or Y₂ represents a heteroatom or a heteroatom group, or Y₂ represents (independently from Z) a divalent group selected from among those which can represent Z (except for arylene); when A or B represent —R₁—Y₂—R₂, this can for example be a group —C₆H₄—, —C₆H₄—C(CH₃)₂—C₆H₄—, C₆H₄—SO₂—C₆H₄—, C₆H₄—CO—C₆H₄— or —C₆H₄—CHOH—C₆H₄—;

or further A and/or B represent a group having the formula

—(EO)m₁—(DO)ₘ—D₁— with E being an alkylene group having 1 to 10 carbon atoms or a hydroxyalkylene having 1 to 10 carbon atoms, D being a divalent hydrocarbon group having 1 to 10 carbon atoms, m₁ being a number equal to 0 or 1, m being a number from 1 to 600, D₁ being identical to E when m₁=1 and identical to D when m₁=0;

or further A and/or B represent a group

—E—O—G—O—E—,

E being defined as above and G being a hydrocarbon, such as an alkylene, cycloalkylene, arylene or aralkylene, which may be substituted, in particular by one or several -OH and/or —O groups; E represents for example —CH₂CH(OH)CH₂— or an alkylene having 1 to 4 carbon atoms;

one of the substituents A or B can further represent, for example, a group having the formula $$-(CH_2)_n, CO-X'_2-CO-(CH_2)_{n'}-$$

in which $X'_2$ represents:

a)

a group $$-O-(CH_2-CH_2-O)_x-CH_2-CH_2-O- \text{ or}$$

$$-O-(CH_2-\underset{CH_3}{CH}-O)_y-CH_2-\underset{CH_3}{CH}-O-$$

where x and y designate an integer from 1 to 4 representing a defined degree of polymerization or any number whatsoever from 1 to 4 representing an average degree of polymerization;

b) a bis-secondary diamine residue such as a residue derived from piperazine;

c) a bis-primary diamine residue having the formula:

$$-NH-Y-NH-$$

where Y designates a bivalent hydrocarbon radical having 2 to 20 carbon atoms, such as a linear or branched alkylene, or the bivalent group $$-CH_2-CH_2-S-S-CH_2-CH_2-; \text{ or}$$

d) a ureylene group having the formula —NH—CO—NH—; and n' designates the number 1 or an integer from 3 to 10;

and in this case the other substituent A or B represents in particular a linear or branched alkylene, which may be unsaturated.

In the present invention, the phrase "lower alkyl (or alkylene)" designates an alkyl (or alkylene) having 1 to 6 carbon atoms.

Polymers of this type are described, in particular, in the following French patents and patent applications: 2,320,330, 2,270,846, 2,316,271, 2,232,563, 2,336,434, 2,389,374, 2,399,451, 2,413,907, 2,471,776, 2,471,777, 2,471,996, 2,471,997; and U.S. Pat. Nos. 2,261,002, 2,271,378, 2,273,780, 2,375,853, 2,388,614, 2,454,547, 3,206,462, 3,734,889, 3,874,870, 4,001,432, 3,929,990, 3,996,904, 4,005,193, 4,025,617, 4,025,627, 4,027,653, 4,026,945 and 4,027,020.

The polycationic polymers which can be used in accordance with the present invention, including those containing units of Formula I, can also be sequenced polymers.

The nitrogenized polycationic polymers, such as defined above, which can be used in accordance with the present invention, have a molecular mass (determined for example using the method of light diffusion with a photogoniodiffusometer: SICA; Wippler and Scheibling apparatus) which is generally greater than 1000. There is no upper fixed limit for the molecular mass, the only limiting condition being that the polymer (in fluoride form) remains soluble in water. As an example, it can be indicated that the polymers which can be used in accordance with the present invention generally have a molecular mass capable of varying from 1000 to 100,000 approximately.

Among the presently preferred polycationic polymers, there can be cited, for example, those in which the units of Formula I have at least one of the following non-mutually exclusive characteristics:

$R_1$, $R_2$, $R_3$, $R_4$ are saturated aliphatic groups having 1–12 carbon atoms;

$R_1$, $R_2$, $R_3$, $R_4$ are alkyl groups having 1–12 carbon atoms;

$$R_1 = R_3 = CH_3;$$

$$R_1 = R_3 = R_4 = CH_3;$$

A and B represent a linear or branched alkylene having 3 to 10 carbon atoms in the chain;

A represents an alkyleneoxyalkylene group having 4 to 12 carbon atoms,
and B represents:

$$-(CH_2)_n-NH-CO-NH-(CH_2)_n$$

or $$-(CH_2)_n-NH-CO-Alk-CO-NH-(CH_2)_n-,$$

with Alk representing an alkylene having 1 to 34 carbon atoms and n being an integer from 1 to 10;

$$R_1 = R_2 = R_3 = R_4 = CH_3,$$

A represents ethyleneoxyethylene and B represents:

either $-(CH_2)_3-NH-CO-NH-(CH_2)_3-,$ or $-(CH_2)_3-NHCO-(CH_2)_4-CONH-(CH_2)_3-,$ or $-(CH_2)_3-NHCO(CH_2)_7-CONH-(CH_2)_3-.$ As indicated above, the dentifrice compositions of the present invention can further contain all the conventional ingredients used in this type of product. They are prepared in accordance with conventional processes. They can in particular contain at least one polishing agent, for example a mineral one. They can also contain a surface active agent.

The surface active agents which can be used can be of the anionic, amphoteric, cationic or non-ionic type. Preferably, cationic surface active agents or non-ionic surface active agents are used.

Among the cationic surface active agents, alkylammonuum compounds (saturated or unsaturated heterocycles) alkenylamines and primary alkylamines, secondary or tertiary alkylamines, tertiary amines, amine ethers and primary, secondary or tertiary alkylene-diamines can be cited.

Among the non-ionic surface active agents, polyoxyethylenated alkylphenols, polyoxyethylenated alcohols, fatty acid polyoxyethylenated esters, polyoxyethylenated alkylamines, polyoxyethylenated alkylamides, glycol or glycerol esters, polyglycerol esters, tetritol esters, pentritol esters, hexitol esters or anhydrohexitol esters, sugar esters, polyoxyalkylenated polyol esters, and copolymers with polyalkylene oxide units (in particular Tergitols and Pluronics) can be cited.

In particular, poly(hydroxypropylether) non-ionic surface active agents can be used which are selected from compounds of Formulae (I), (II) and (III) below and/or from among the compounds prepared in accordance with the process described in paragraph (iv) below:

(i)

where $R'_6$ designates an alkyl group or a mixture of alkyl groups containing 10 to 14 carbon atoms and z is an integer or a decimal number from 2 to 10 and preferably from 3 to 6;

(ii)

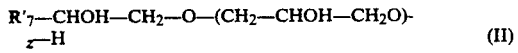

where $R'_7$ designates an alkyl group or a mixture of alkyl groups having from 8 to 12 carbon atoms and $z'$ designates an integer or a decimal number from 2 to 10 and preferably from 2.5 to 6;

(iii)

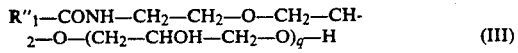

where $R''_1$ designates an alkyl and/or alkenyl group or mixture or alkyl and/or alkenyl groups having from 11 to 18 carbon atoms, and q designates an integer or a decimal number from 1 to 5 and preferably from 1.5 to 4;

(iv) the compounds prepared by condensation, using acid catalysis, from 2 to 10 and preferably from 2.5 to 6 moles of glycidol per mole of alcohol or alkane-diol-1,2 containing 10 to 14 carbon atoms. The process for preparing these compounds is described in French Patent 2,169,787.

These particular non-ionic surface active agents are described, in particular, in French patent applications 1,477,048, 2,091,516 and 2,328,763.

The surface active agents of the present invention are present in an amount ranging from 0 to 20% by weight relative to the total weight of the composition and generally, when they are present, in an amount ranging from 0.5 to 5%.

The present invention also relates to a dentifrice composition, such as defined above, containing no cationic surface active agent. Such a composition, for example, contains as the surface active agent, at least one non-ionic surface active agent such as defined above.

As indicated above, the compositions of the present invention can contain a polishing agent. A particular embodiment of the present invention is a dentifrice composition containing a polishing agent, in particular a mineral polishing agent. The polishing agents are abrasive agents which are compatible with use in dentifrice compositions. Examples of such polishing agents will be given below.

As has been indicated above, the polycationic polymer fluorides which, can be used in accordance with the present invention have antibacterial activity. However, there can be added to the dentifrice composition other cationic compounds of an antibacterial nature, such as for example diisobutyl phenoxyethoxy ethyl dimethyl benzyl ammonium chloride (Hyamine 1622), dodecyl trimethyl ammonium bromide, dodecyl dimethyl (2-phenoxyethyl) ammonium bromide, benzyl dimethyl stearyl ammonium chloride, cetyl pyridinium chloride, quaternized 5-amino 1,3 bis (2-ethylhexyl) hexyl)- 5 methyl hexahydroxypyrimidine, trimethyl cetyl ammonium bromide, alkyl dimethyl hydroxyethyl ammonium bromide (with alkyl = coprah residue), chlorhexidine, alexidine and cationic aliphatic tertiary amines.

These additional antibacterial agents, when they are present, can represent up to 10% of the total weight of the dentifrice composition. Preferably these compounds will be used in concentrations of between 0.05 and 2%.

The present invention also relates, in particular, to dentifrice compositions, such as defined above, containing no additional cationic antibacterial agents, and in particular dentifrice compositions which, in addition, contain no cationic surface active agent; and, among these compositions, those which contain a polishing agent, particularly a mineral polishing agent.

The dentifrice compositions in accordance with the present invention can be provided in the form of pastes, gels, chewing gum, powders or mouthwashes.

The pastes generally contain a mineral abrasive polishing agent composed of one or several compounds which are largely insoluble in water; there can be cited, for example, sodium or potassium metaphosphates, dihydrated calcium phosphate, dicalcium phosphate, tricalcium phosphate, calcium pyrophosphate, alumina, hydrated aluminum and, in particular, trihydrated alumina, silica, aluminum or zirconium silicates, bentonite, as well as magnesium orthophosphate or trimagnesium phosphate.

In the case of transparent gels, a polishing agent based on colloidal silica or alkali metal or alkaline earth metal aluminosilicates, preferably sodium or calcium, will be used for example.

In addition to the active ingredients, the chewing gums principally contain at least one natural or synthetic chewable gum, aromatization agents, sweetening agents, moistening agents, bactericidal agents and preserving agents.

Among the gums having sufficient plasticity (alone or mixed) to be chewable, sodium carboxymethylcellulose and gum tragacanth can be cited.

The chewing gums generally contain from 0.5 to 70% by weight of chewable gum.

The polishing agents which can be used in the chewing gums can be of mineral or organic origin. These are, for example, calcium carbonate, magnesium carbonate, sodium carbonate, calcium phosphates and sulfates, alumina and hydrated alumina, silica, magnesium oxide, magnesium hydroxide, magnesium trisilicate and magnesium pyrophosphate, or cellulose compounds obtained by grinding cereal grains.

The polishing agents represent 10 to 80%, and preferably 15 to 65%, of the total weight of the composition.

Cohesion agents, which can be natural gums or synthetic thickening agents, can also be added to the dentifrice compositions in accordance with the present invention.

As natural gums, gum tragacanth, xanthan gums, guar gums, carob gums or carrageenan gums can be cited.

As synthetic thickening agents, cellulose derivatives, such as the sodium salt of carboxymethyl cellulose, methylcellulose or hydroxyalkylcelluloses are essentially used.

These cohesion agents, when they are present in the dentifrice compositions in accordance with the invention, are generally incorporated in an amount by weight of up to 10% and preferably between 0.5 and 3%.

The compositions in the form of mouthwashes are liquid dentifrice compositions, which essentially contain an aqueous solution of a foaming agent, and optionally a thickening agent, bactericidal agents, sweeteners and aromatizing substances. These liquid compositions can further contain small quantities of an ultra-fine polishing agent.

The dentifrice compositions in powder form essentially contain a polishing agent and a foaming agent.

In general, there is also added to the dentifrice compositions a sweetening agent, such as for example saccharose, lactose, fructose, xylitol, sodium cyclamate, maltose or sodium saccharinate, in concentrations generally ranging up to 2%, and varying for example between 0.1 and 2% of the total weight of the composition.

To ensure good bacteriological purity of the formulations in accordance with the present invention, it is also possible to use a preserving agent such as those which are currently used in this type of product: formol and its derivatives, methyl parahydroxybenzoate, propyl parahydroxybenzoate, etc. These products can be present in an amount ranging up to 0.5% and varying for example from 0.01 to 0.5% by weight.

Most of the time, an aromatizing substance will be added to the dentifrice composition in an amount which can generally range up to 5%, and varying for example between 0.5 and 5% relative to the total weight of the composition: mint, anise, eucalyptus, cinnamon, clove, sage, or licorice essences, fruit essences such as lemon, orange, mandarin and strawberry, or optionally, methyl salicylate.

The pH of the dentifrice composition measured in the conventional manner for a dispersion with 20% paste in water is generally between 4.5 and 9.

The preferred pH range is situated between 5.5 and 8.5.

Alkaline pH's are generally used only in the case of unstable raw materials in a neutral or acid medium. This, for example, is the case of dentifrices using calcium carbonate as the polishing agent.

In the majority of cases, the pH can be adjusted by means of a pH-modifying agent such as, for example, citric acid, benzoic acid, or monosodium or disodium phosphates.

A further object of the present invention is the use, in dentifrice compositions containing mineral polishing agents and surface active agents, of polycationic polymer fluorides as anti-caries agents.

The dentifrice compositions of the present invention are used in humans in accordance with the usual methods.

The following examples illustrate the invention without, however, limiting it. In these examples, the following designations are used:

polycationic fluoride A: an ionene based on units of Formula I, with $R_1=R_2=R_3=R_4=CH_3$, $A=(CH_2)_6$, $B=(CH_2)_3$, such that 90% of $X^-$ are fluoride ions and 10% chloride ions;

compound B: Satiagum VZ 40 (sold by CECA-SATIA) which is a carrageenan and alginate complex,
compound C: the compound of formula:

$$R-CHOH-CH_2O-[CH_2-CHOH-CH_2O]-_nH$$

in which
$R=C_{9-12}$ alkyl and
$n=3.4$;

polycationic fluoride D: an ionene based on units of formula I, with $R_1=R_3=CH_3$, $R_2=R_4=C_3H_7$, $A=(CH_2)_3$, $B=(CH_2)_4$, such that 80% of $X^-$ are fluoride ions and 20% are chloride ions;

compound E: Satiagum HE 41 (sold by CECA-SATIA) which is a carrageenan/alginate complex;

compound F: VEEGUM (sold by Vanderbilt) which a magnesium and aluminum silicate;

compound G: the compound of formula:

$$C_{12}H_{25}-O-[C_2H_3(CH_2OH)O]_nH;$$

polycationic fluoride H: ionene based on units of Formula I, with $R_1=R_2=R_3=R_4=CH_3$, $A=B=(CH_2)_{10}$, such that 100% of the $X^-$ are fluoride ions;

polycationic fluoride J: ionene based on units of Formula I, with $R_1=R_3=CH_3$, $R_2=R_4=C_4H_9$, $A=B=(CH_2)_{10}$, such that 5% of the $X^-$ are fluoride ions, the remainder being chlorides;

polycationic fluoride K: ionene based on units of Formula I, with $R_1=R_3=CH_3$, $R_2=R_4=C_6H_{13}$, $A=B=(CH_2)_{10}$, such that 50% of the $X^-$ are fluoride ions, the remaining 50% being chlorides;

polycationic fluoride L: ionene having units of Formula I wherein $R_1=R_3=CH_3$, $R_2=R_4=R_8H_{17}$, $A=B=(CH_2)_{10}$, such that 80% of the $X^-$ are fluoride ions, the remaining 20% being chlorides; and polycationic fluoride M: ionene having units of Formula I, with $R_1=R_3=CH_3$, $R_2=C_{12}H_{25}$, $A=B=(CH_2)_{10}$, such that 90% of the $X^-$ are fluoride ions, the remainder being chlorides;

EXAMPLE 1

A dentifrice paste was prepared having the following composition:

| | |
|---|---|
| Polycationic fluoride A | 1.0 g |
| Trihydrated alumina | 55 g |
| Glycerin | 20 g |
| Compound B | 0.8 g |
| Compound C | 1 g |
| Mentholated flavoring | 0.9 g |
| Water quantity sufficient for | 100 g |

A dentifrice paste of similar composition was also prepared, but the polycationic fluoride A w as replace with polycationic fluoride H.

EXAMPLE 2

A dentifrice paste was prepared having the following composition:

| | |
|---|---|
| Polycationic fluoride A | 0.8 g |
| Polycationic fluoride D | 0.2 g |
| Non-ionic surface active agent* | 2 g |
| Ethanol | 3 g |

-continued

| Sorbitol | 23 g |
| Dicalcium phosphate dihydrate | 45 g |
| Compound E | 0.4 g |
| 1-6 di(4-chlorophenyl biguanido) hexane gluconate | 0.3 g |
| Strawberry flavoring | 1 g |
| Water quantity sufficient for | 100 g |

*Polyoxyethylene-polyoxybutylene copolymer in which the molecular weight of the polyoxybutylene residue is 1200 with a polyoxyethylene content of approximately 80%

A similar dentifrice paste was prepared replacing the polycationic fluoride A with polycationic fluoride J.

EXAMPLE 3

A dentifrice paste having the following composition was prepared:

| Polycationic fluoride A | 0.5 g |
| Sodium monofluorophosphate | 0.3 g |
| Amido lauryl betaine fatty acids of copra | 1.7 g |
| Microcrystalline aluminum hydroxide | 43.5 g |
| Glycerin | 27 g |
| Propylene glycol | 1.5 g |
| Gum tragacanth | 0.5 g |
| Anise flavoring | 1.1 g |
| Monosodium phosphate quantity sufficient for | pH 7 |
| Water quantity sufficient for | 100 g |

A similar dentifrice paste was also prepared replacing the polycationic fluoride A with polycationic fluoride K.

EXAMPLE 4

A dentifrice paste having the following composition was prepared:

| Polycationic fluoride D | 1 g |
| Micronized silica | 25 g |
| Glycerin | 25 g |
| Xanthan gum | 1.3 g |
| Licorice flavoring | 1.2 g |
| Saccharin | 0.15 g |
| Polyoxyethylene sorbitan monolaurate | 2 g |
| Hexachlorophene | 0.03 g |
| Water quantity sufficient for | 100 g |

A similar dentifrice paste was also prepared replacing the polycationic fluoride D with polycationic fluoride L.

EXAMPLE 5

A dentifrice paste having the following composition was prepared:

| Polycationic fluoride A | 0.4 g |
| Sodium fluoride | 0.1 g |
| Dicalcium phosphate dihydrate | 33 g |
| Dicalcium phosphate | 10 g |
| Calcium carbonate | 4 g |
| Glycerin | 23 g |
| Saccharin | 0.15 g |
| Compound B | 0.8 g |
| Compound C | 1.3 g |
| Compound F | 0.5 g |
| Lemon essence | 1.3 g |
| Water quantity sufficient for | 100 g |

A similar dentifrice paste was prepared replacing the polycationic fluoride A with polycationic fluoride M.

EXAMPLE 6

A liquid dentifrice composition having the following composition was prepared:

| Polycationic fluoride D | 0.4 g |
| Saccharin | 0.03 g |
| Ethanol | 25 g |
| Glycerin | 10 g |
| Compound G | 1 g |
| Water quantity sufficient for | 100 g |

A similar liquid dentifrice composition was prepared replacing the polycationic fluoride D with polycationic fluoride L.

What is claimed is:

1. A dentifrice composition containing, as an anti-caries agent, at least one water-soluble polycationic polymer having is part of the macrochain and having at least 5% of the cationic charges balanced by fluoride anions, said polycationic polymer comprising units of formula I

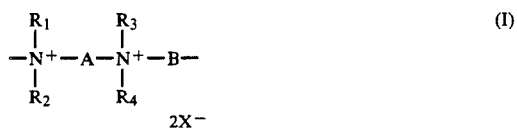

wherein
$R_1$, $R_2$, $R_3$ and $R_4$, each independently, represent an aliphatic, alicyclic or arylaliphatic group, optionally substituted, containing a maximum of 20 carbon atoms, or a hydroxyaliphatic group having 1–8 carbon atoms; or one or both of the pairs of substituents, $R_1$ and $R_2$, and $R_3$ and $R_4$, attached to a same nitrogen atom represent together a divalent group forming, with the nitrogen atom to which they are attached, a heterocycle capable of containing one or more heteroatoms other than nitrogen; or one or both of the pairs, $R_1$ and $R_3$, and $R_2$ and $R_4$, together form a divalent group linking two consecutive nitrogen atoms, represented in the unit of formula I, to which they are attached respectively;

A and B, each independently, represent (1) linear or branched alkylene having 1–20 carbon atoms, optionally unsaturated, the said alkylene group being able to be substituted and/or interrupted by one or more heteroatoms, and/or by one or more heteroatomic groups and/or by one or more aliphatic or aromatic rings or by one or more heterocycles; (2) a cycloalkylene group, optionally substituted and/or optionally having double bonds, containing up to 20 carbon atoms; (3) one or more arylene groups having 6 to 20 carbon atoms, the said arylene groups being optionally substituted and/or separated by one or more heteroatoms and/or by one or more heteroatomic groups or by one or more alkylene groups and/or by one or more aliphatic rings and/or by one or more heterocycles; and $X^-$ represents an anion, with the proviso that in the said composition at least 5%, in number, of the anions present in the polycationic polymer, having units of formula I, are fluoride ions.

2. The composition of claim 1 wherein said polycationic polymer is an ionene having units of formula I wherein $R_1=R_2=R_3=R_4=CH_3$; A is $(CH_2)_6$; B is ($CH_2$)$_3$ and that 90% of $X^-$ are fluoride ions and 10% are chloride ions.

3. The composition of claim 1 wherein said polycationic polymer is an ionene having units of formula I wherein $R_1=R_3=CH_3$; $R_2=R_4=C_3H_7$; $A=(CH_2)_3$; $B=(CH_2)_4$ and that 80% of $X^-$ are fluoride ions and 20% are chloride ions.

4. The composition of claim 1 wherein said polycationic polymer is an ionene having units of formula I wherein $R_1=R_2=R_3=R_4=CH_3$; $A=B=(CH_2)_{10}$ and that 100% of $X^-$ are fluoride ions.

5. The composition of claim 1 wherein said polycationic polymer is an ionene having units of formula I wherein $R_1=R_3=CH_3$; $R_2=R_4=C_4H_9$; $A=B=(CH_2)_{10}$ and that 5% of $X^-$ are fluoride ions, the remainder being chloride ions.

6. The composition of claim 1 wherein said polycationic polymer is an ionene having units of formula I wherein $R_1=R_3=CH_3$; $R_2=R_4=C_6H_{13}$; $A=B=(CH_2)_{10}$ and 50% of $X^-$ are fluoride ions, the remainder being chloride ions.

7. The composition of claim 1 wherein said polycationic polymer is an ionene having units of formula I wherein $R_1=R_3=CH_3$; $R_2=R_4=C_8H_{17}$; $A=B=(CH_2)_{10}$ and 80% of $X^-$ are fluoride ions, the remainder being chloride ions.

8. The composition of claim 1 wherein said polycationic polymer is an ionene having units of formula I wherein $R_1=R_3=CH_3$; $R_2=R_4=C_{12}H_{25}$; $A=B=(CH_2)_{10}$ and 90% of $X^-$ are fluoride ions, the remainder being chloride ions.

9. A dentifrice composition containing, as an anti-caries agent, at least one water-soluble polycationic polymer comprising units of formula I

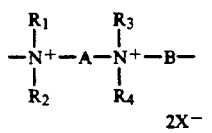
(I)

said polycationic polymer being selected from the group consisting of
(1) an ionene having units of formula I wherein $R_1=R_2=R_3=R_4=CH_3$; A is $(CH_2)_6$; B is $(CH_2)_3$ and that 90% of $X^-$ are fluoride ions and 10% are chloride ions;
(2) an ionene having units of formula I wherein $R_1=R_3=CH_3$; $R_2=R_4=C_3H_7$; $A=(CH_2)_3$; $B=(CH_2)_4$ and that 80% of $X^-$ are fluoride ions and 20% are chloride ions;
(3) an ionene having units of formula I wherein $R_1=R_2=R_3=R_4=CH_3$; $A=B=(CH_2)_{10}$ and that 100% of $X^-$ are fluoride ions;
(4) an ionene having units of formula I wherein $R_1=R_2=CH_3$; $R_2=R_4=C_4H_9$; $A=B=(CH_2)_{10}$ and that 5% of $X^-$ are fluoride ions, the remainder being chloride ions;
(5) an ionene having units of formula I wherein $R_1=R_3=CH_3$; $R_2=R_4=C_6H_{13}$; $A=B=(CH_2)_{10}$ and 50% of $X^-$ are fluoride ions, the remainder being chloride ions;
(6) an ionene having units of formula I wherein $R_1=R_2=CH_3$; $R_2=R_4=C_8H_{17}$; $A=B=(CH_2)_{10}$ and 80% of $X^-$ are fluoride ions, the remainder being chloride ions; and
(7) an ionene having units of formula I wherein $R_1=R_3=CH_3$; $R_2=R_4=C_{12}H_{25}$; $A=B=(CH_2)_{10}$ and 90% of $X^-$ are fluoride ions, the remainder being chloride ions.

10. A dentifrice composition containing, as an anti-caries agent, at least one water-soluble polycationic polymer comprising units of formula I

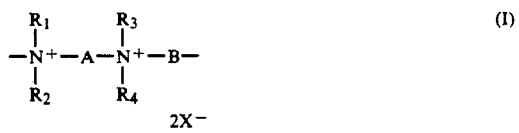

wherein
$R_1$, $R_2$, $R_3$ and $R_4$, each independently, represent an aliphatic group containing a maximum of 20 carbon atoms;
A and B, each independently, represent linear or branched alkylene having 1-20 carbon atoms and
$X^-$ represents an anion, with the proviso that in said composition at least 5%, in number, of the anions present in said polycationic polymer, having units of formula I, are fluoride ions.

11. The composition of claim 1 wherein the said units of formula I have at least one of the following non-mutually exclusive characteristics:
$R_1$, $R_2$, $R_3$ and $R_4$ are saturated aliphatic groups having 1-12 carbon atoms;
$R_1$, $R_2$, $R_3$ and $R_4$ are alkyl groups having 1-12 carbon atoms;
$R_1$ and $R_3$ are $CH_3$;
$R_1$, $R_3$ and $R_4$ are $CH_3$;
A and B represent linear or branched alkylene having 3 to 10 carbon atoms in the chain;
A represents an alkyleneoxyalkylene group having 4 to 12 carbon atoms and B represents $—(CH_2)_n—NH—CO—NH—(CH_2)_n—$ or $—(CH_2)_n—NH—CO—Alk—CO—NH—(CH_2)_n—$, wherein Alk represents alkylene having 1-34 carbon atoms, and n is a whole number between 1 to 10;
$R_1$, $R_2$, $R_3$ and $R_4$ are $CH_3$, A represents ethyleneoxyethylene and B represents $—(CH_2)_3—NH—CO—NH—(CH_2)_3—$, $—(CH_2)_3—NH—CO—(CH_2)_4—CONH—(CH_2)_3—$ or $—(CH_2)_3—NHCO—(CH_2)_7—CONH—(CH_2)_3—$.

12. The composition of claim 1 wherein said polycationic polymer is present in an amount ranging from 0.1 to 5 percent by weight based on the total weight of said composition.

13. The composition of claim 1 wherein said polycationic polymer is present in an amount ranging from 0.5 to 5 percent by weight based on the total weight of said composition.

14. The composition of claim 1 which also included a polishing agent.

15. The composition of claim 1 which also includes a mineral polishing agent.

16. The composition of claim 1 which is free from a cationic surface active agent.

17. The composition of claim 1 which is free from a complementary cationic antibacterial agent.

18. A method for preventing tooth decay comprising applying to the tooth an effective amount of the dentifrice composition of claim 1.

19. The method of claim 18 wherein said dentifrice composition contains a polishing agent.

20. The method of claim 19 wherein said polishing agent is a mineral polishing agent.

21. The method of claim 18 wherein said dentifrice composition is free from a cationic surface active agent.

22. The method of claim 18 wherein said dentifrice composition is free from a complementary cationic anti-bacterial agent.

* * * * *